United States Patent
Brack

[11] 3,971,807
[45] July 27, 1976

[54] CATIONIC DYESTUFFS

[75] Inventor: Alfred Brack, Odenthal, Germany

[73] Assignee: Bayer Aktiengesellschaft, Leverkusen, Germany

[22] Filed: Dec. 6, 1974

[21] Appl. No.: 530,444

[30] Foreign Application Priority Data
Dec. 6, 1973 Germany............................ 2360876

[52] U.S. Cl.............................. 260/326.9; 260/37 N; 260/313.1
[51] Int. Cl.².......................................... C07D 209/56
[58] Field of Search............. 260/313.1, 37 N, 326.9

[56] References Cited
UNITED STATES PATENTS
3,769,297 10/1973 Brack et al. ..................... 260/326.9
3,853,913 12/1974 Brack et al. ......................... 260/315

*Primary Examiner*—Paul M. Coughlan, Jr.
*Attorney, Agent, or Firm*—Plumley and Tyner

[57] ABSTRACT
Cationic dyestuffs of the formula

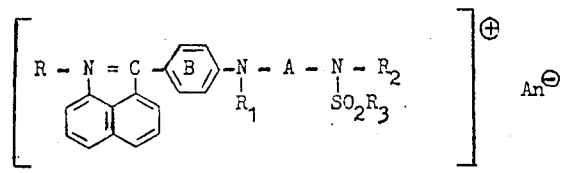

in which
R represents an alkyl or alkenyl radical or an alkylene radical bonded to the -position of the naphthalene ring;
$R_1$ represents hydrogen, an alkyl or alkenyl radical or an alkylene radical bonded to the ring B in the 0-position;
$R_2$ represents hydrogen or an alkyl, alkenyl, cycloalkyl, aralkyl, aryl or heteryl radical;
$R_3$ represents an alkyl, alkenyl, cycloalkyl, aralkyl, aryl or heteryl radical or a disubstituted amino group or $R_2$ and $R_3$ conjointly represent the radical of a cyclic sulphonamide;
A represents an alkylene radical with 2 to 4 C atoms and
An $^{(-)}$ represents an anion
and in which the cyclic and acyclic radicals can contain nonionic substituents and the ring B can contain a fused benzoring, are suitable for dyeing and printing of natural and synthetic materials especially acrylonitrile and acid modified polyesters and polyamides.

7 Claims, No Drawings

CATIONIC DYESTUFFS

The invention relates to new cationic dyestuffs of the formula

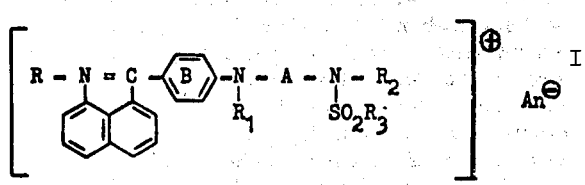

in which
R represents an alkyl or alkenyl radical or an alkylene radical bonded to the β-position of the naphthalene ring,
$R_1$ represents hydrogen, an alkyl or alkenyl radical or an alkylene radical bonded to the ring B in the 0-position,
$R_2$ represents hydrogen or an alkyl, alkenyl, cycloalkyl, aralkyl, aryl or heteryl radical,
$R_3$ represents an alkyl, alkenyl, cycloalkyl, aralkyl, aryl or heteryl radical or a disubstituted amino group or $R_2$ and $R_3$ conjointly represent the radical of a cyclic sulphonamide,
A represents an alkylene radical with 2 to 4 C atoms and
An $^{(-)}$ represents an anion
and in which the cyclic and acyclic radicals can contain nonionic substituents and the ring B can contain a fused benzoring, and also processes for the preparation of these dyestuffs and their use for dyeing, printing and bulk dyeing of natural and synthetic materials.

The following may be mentioned as examples of R, $R_1$, $R_2$ and $R_3$: as alkyl radicals, above all $C_1$–$C_6$-alkyl radicals, such as the methyl, ethyl, n- and i-propyl, n-, sec.- and t-butyl radical and the n- and i-amyl and n-hexyl radical, and also $C_1$–$C_6$-alkyl radicals which are substituted by non-ionic substituents, especially by halogen atoms, $C_1$–$C_4$-alkoxy, nitrile, $C_1$–$C_4$-alkoxycabonyl or carbonamide groups, such as the chloromethyl, 2-chloroethyl, 2-methoxyethyl, 2-ethoxyethyl, 2-cyanoethyl, 2-methoxycarbonylethyl and 2-ethoxycarbonylethyl radical; as alkenyl radicals, above all $C_3$–$C_6$-alkenyl radicals, such as the allyl, methallyl and hexen-1-yl-6 radical, and $C_3$–$C_6$-alkenyl radicals substituted by non-ionic substituents, especially by halogen atoms, such as the 2-chloroallyl radical.

The following may be mentioned as examples of $R_2$ and $R_3$: as cycloalkyl radicals, above all the cyclopentyl and cyclohexyl radical and their derivatives substituted by non-ionic substituents, especially halogen atoms and $C_1$–$C_4$-alkyl groups, such as the 4-chloro-cyclohexyl, dimethyl-cyclohexyl and t-butyl-cyclohexyl radical; as aralkyl radicals, above all the benzyl, 2-phenylethyl and 2-phenylpropyl-(2) radical and their derivatives substituted in the phenyl nucleus by non-ionic substituents, especially by halogen atoms, $C_1$–$C_4$-alkyl groups or $C_1$–$C_4$-alkoxy groups, such as the 3- or 4-chlorobenzyl, 3-methylbenzyl, 4-methoxybenzyl and 3,4-dimethylbenzyl radical; as aryl radicals, above all the phenyl radical and phenyl radicals substituted by non-ionic substituents, especially halogen atoms or $C_1$–$C_4$-alkyl, $C_1$–$C_4$-alkoxy, nitro and nitrile groups, such as the 3- and 4-chlorophenyl, tolyl, 4-t-butylphenyl, 4-methoxyphenyl, 3-ethoxyphenyl, 2-nitrophenyl, 4-cyanophenyl or 4-nitrophenyl radical; as heteryl radicals, radicals of heterocyclic structures of aromatic character, especially 5- and 6-membered heterocyclic structures, such as the pyridine, pyrimidine, triazine, triazole, thiazole, imidazole and tetrazole radical.

Radicals of cyclic sulphonamides which can be formed by $R_2$ and $R_3$ together with the sulphonyl group and the nitrogen atom are above all the radicals of 4-, 5- and 6-membered sultams, especially propanesultam and butanesultam.

Possible disubstituted amino groups $R_3$ are above all dialkylamino groups, especially $C_1$–$C_4$-dialkylamino groups, such as the dimethylamino, diethylamino, di-n-propylamino, di-n-butylamino and di-sec.-butylamino group, and also the morpholino, piperidino and piperazino group.

As alkylene radicals there may above all be mentioned: for R, the ethylene radical; for $R_1$, the radicals $-CH_2-CH_2-$ and $-(CH_2)_3-$ and the alkyl derivatives $-CH_2-CH(CH_3)-CH(CH_3)$ and $-CH_2-CH_2-CH(CH_3)-$ derived therefrom; for A, the radicals $-CH_2-CH_2-$, $-(CH_2)_3-$ and $-(CH_2)_4-$ and the alkyl derivatives $-CH_2-CH(CH_3)-CH(CH_3)-$ and $-CH_2-CH_2-CH(CH_3)-$ derived therefrom.

Within the scope of the present invention, "non-ionic substituents" are understood as the radicals customary in dyestuff chemistry which do not dissociate anionically. As examples there may be mentioned: $C_1$–$C_4$-alkoxy groups, such as methoxy, ethoxy, n- and iso-propoxy, butoxy, β-methoxyethoxy, β-cyanoethoxy and allyloxy groups; halogen atoms such as fluorine, chlorine and bromine; amino groups as well as amino groups substituted by $C_1$–$C_4$-alkyl, aryl, acyl or benzyl, such as acetylamino, methylsulphonylamino, phenylsulphonylamino, dimethylamino, phenylamino and benzylamino groups; sulphonyl groups, such as methylsulphonyl and phenylsulphonyl groups; carboxylic acid derivatives, such as methoxycarbonyl, ethylcarbonyl, carbamoyl and nitrile groups and (on rings) $C_1$–$C_4$-alkyl groups, such as are, for example, mentioned later for R.

Possible anions $An^{(-)}$ are the organic and inorganic anions customary for cationic dyestuffs.

Examples of inorganic anions are fluoride, chloride, bromide and iodide, perchlorate, hydroxyl, radicals of acids containing S, such as bisulphate, sulphate, disulphate and aminosulphate; radicals of nitrogen-oxygen acids, such as nitrate; radicals of oxygen acids of phosphorus, such as dihydrogen phosphate, hydrogen phosphate, phosphate and metaphosphate; radicals of carbonic acid, such as bicarbonate and carbonate; further anions of oxygen acids and complex acids, such as methosulphate, ethosulphate, hexafluosilicate, cyanate, thiocyanate, ferrocyanide, ferricyanide, trichlorozincate and tetrachlorozincate, tribromozincate and tetrabromozincate, stannate, borate, divanadate, tetravanadate, molybdate, tungstate, chromate, bichromate and tetrafluoborate, as well as anions of esters of boric acid, such as of the glycerol ester of boric acid, and of esters of phosphoric acid, such as of methylphosphate.

Examples of organic anions are anions of saturated or unsaturated aliphatic, cycloaliphatic, aromatic and heterocyclic carboxylic acids and sulphonic acids, such as radicals of acetic acid, chloroacetic acid, cyanoacetic acid, hydroxyacetic acid, aminoacetic acid, methylaminoacetic acid, aminoethylsulphonic acid, methylaminoethylsulphonic acid, propionic acid, n- butyric acid, iso-butyric acid, 2-methyl-butyric acid, 2-ethyl-butyric acid, dichloroacetic acid, trichloroacetic acid, trifluoroacetic acid, 2-chloropropionic acid, 3-chloropropionic acid, 2-chlorobutyric acid, 2-hydroxypropionic acid, 3-hydroxypropionic acid, o-ethylglycollic acid, thioglycollic acid, glyceric acid, malic acid, dodecyl-tetraethylene glycol-ether-propionic acid, 3-(nonyloxy)-propionic acid, 3-(isotridecyloxy)-propionic acid, 3-(isotridecyloxy)-diethylene glycol-ether-propionic acid, the ether-propionic acid of the alcohol mixture with 6 to 10 carbon atoms, thioacetic acid, 6-benzoylamino-2-chlorocaproic acid, nonylphenol-tetraethylene glycol-ether-propionic acid, nonylphenol-diethylene glycol-ether-propionic acid, dodecyl-tetraethylene glycol-ether-propionic acid, phenoxyacetic acid, nonylphenoxyacetic acid, n-valeric acid, iso-valeric acid, 2,2,2-trimethylacetic acid, n-caproic acid, 2-ethyl-n-caproic acid, stearic acid, oleic acid, ricinoleic acid, palmitic acid, n-pelargonic acid, lauric acid, a mixture of aliphatic carboxylic acids with 9 to 11 carbon atoms (Versatic Acid 911 from SHELL), a mixture of aliphatic carboxylic acids with 15 to 19 carbon atoms (Versatic Acid 1519 from SHELL), coconut fatty acid first runnings, undecanecarboxylic acid, n-tridecanecarboxylic acid and a coconut fatty acid mixture; acrylic acid, methacrylic acid, crotonic acid, propargylic acid, oxalic acid, malonic acid, succinic acid, glutaric acid, adipic acid, pimelic acid, suberic acid, azelaic acid, the isomer mixture of 2,2,4- and 2,4,4-trimethyladipic acid, sebacic acid, isosebacic acid (isomer mixture), tartaric acid, citric acid, glyoxylic acid, dimethyl ether-$\alpha,\alpha'$-dicarboxylic acid, methylene-bis-thioglycollic acid, dimethyl sulphide-$\alpha,\alpha$-dicarboxylic acid, 2,2'-dithio-di-n-propionic acid, fumaric acid, maleic acid, itaconic acid, ethylene-bisiminoacetic acid, nitrilosulphonic acid, methanesulphonic acid, ethanesulphonic acid, chloromethanesulphonic acid, 2-chloroethanesulphonic acid and 2-hydroxyethanesulphonic acid and Mersolat, that is to say $C_8$–$C_{15}$ paraffinsulphonic acid, obtained by hydrolysing the sulphochlorination products of the corresponding n-paraffins.

Examples of suitable anions of cycloaliphatic carboxylic acids are the anions of cyclohexanecarboxylic acid and cyclohexane-3-carboxylic acid and examples of anions of araliphatic monocarboxylic acids are anions of phenylacetic acid, 4-methylphenylacetic acid and mandelic acid.

Suitable anions of aromatic carboxylic acids are, for example, the anions of benzoic acid, 2-methylbenzoic acid, 3-methylbenzoic acid, 4-methylbenzoic acid, 4-tert.-butylbenzoic acid, 2-bromobenzoic acid, 2-chlorobenzoic acid, 3-chlorobenzoic acid, 4-chlorobenzoic acid, 2,4-dichlorobenzoic acid, 2,5-dichlorobenzoic acid, 2-nitrobenzoic acid, 3-nitrobenzoic acid, 4-nitrobenzoic acid, 2-chloro-4-nitrobenzoic acid, 6-chloro-3-nitrobenzoic acid, 2,4-dinitrobenzoic acid, 3,4-dinitrobenzoic acid, 3,5-dinitrobenzoic acid, 2-hydroxybenzoic acid, 3-hydroxybenzoic acid, 4-hydroxybenzoic acid, 2-mercaptobenzoic acid, 4-nitro-3-methylbenzoic acid, 4-aminobenzoic acid, 5-nitro-2-hydroxybenzoic acid, 3-nitro-2-hydroxybenzoic acid, 4-methoxybenzoic acid, 3-nitro-4-methoxybenzoic acid, 4-chloro-3-hydroxybenzoic acid, 3-chloro-4-hydroxybenzoic acid, 5-chloro-2-hydroxy-3-methyl-benzoic acid, 4-ethylmercapto-2-chlorobenzoic acid, 2-hydroxy-3-methylbenzoic acid, 6-hydroxy-3-methyl-benzoic acid, 2-hydroxy-4-methylbenzoic acid, 6-hydroxy-2,4-dimethylbenzoic acid, 6-hydroxy-3-tert.-butylbenzoic acid, phthalic acid, tetrachlorophthalic acid, 4-hydroxyphthalic acid, 4-methoxyphthalic acid, isophthalic acid, 4-chloroisophthalic acid, 5-nitroisophthalic acid, terephthalic acid, nitroterephthalic acid and diphenyl-3,4-carboxylic acid, o-vanillic acid, 3-sulphobenzoic acid, benzene-1,2,4,5-tetracarboxylic acid, naphthalene-1,4,5,8-tetracarboxylic acid, biphenyl-4-carboxylic acid, abietic acid, phthalic acid mono-n-butyl ester, terephthalic acid monomethyl ester, 3-hydroxy-5,6,7,8-tetrahydronaphthalene-2-carboxylic acid, 2-hydroxy-1-napthoic acid and anthraquinone-2-carboxylic acid.

Examples of suitable anions of heterocyclic carboxylic acids are the anions of pyromucic acid, dehydromucic acid and indolyl-3-acetic acid.

Examples of suitable anions of aromatic sulphonic acids are the anions of benzenesulphonic acid, benzene-1,3-disulphonic acid, 4-chlorobenzenesulphonic acid, 3-nitrobenzenesulphonic acid, 6-chloro-3-nitrobenzenesulphonic acid, toluene-4-sulphonic acid, toluene-2-sulphonic acid, toluene-$\omega$-sulphonic acid, 2-chlorotoluene-4-sulphonic acid, 1-hydroxybenzenesulphonic acid, n-dodecylbenzenesulphonic acid, 1,2,3,4-tetrahydronaphthalene-6-sulphonic acid, napthalene-1-sulphonic acid, naphthalene-1,4- or -1,5-disulphonic acid, napthalene-1,3,5-trisulphonic acid, 1-napthol-2-sulphonic acid, 5-nitronapthalene-2-sulphonic acid, 8-aminonapthalene-1-sulphonic acid, stilbene-2,2'-disulphonic acid and biphenyl-2-sulphonic acid.

An example of a suitable anion of a heterocyclic sulphonic acid is the anion of quinoline-5-sulphonic acid.

Further anions which can be used are those of arylsulphinic, arylphosphonic and arylphosphonous acids, such as benzenesulphinic acid and benzenephosphonic acid.

Colourless anions are preferred. For dyeing from an aqueous medium, anions which do not excessively impair the solubility of the dyestuff in water are preferred. For dyeing from organic solvents, anions which assist the solubility of the dyestuff in organic solvents or at least do not influence it adversely are frequently also preferred.

The anion is in general decided by the preparation process and by the purification of the crude dyestuff which may be carried out. In general the dyestuffs are in the form of halides (especially chlorides or bromides) or methosulphates, ethosulphates, sulphates, benzenesulphonates or toluenesulphonates, or acetates. The anions can be replaced by other anions in a known manner.

Amongst the dyestuffs of the formula I, preferred dyestuffs are those which correspond to the formula

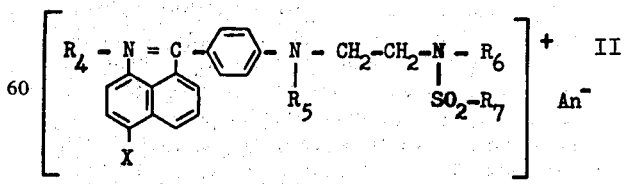

in which $R_4$ represents a $C_1$–$C_4$-alkyl radical which is optionally substituted by a nitrile or $C_1$–$C_4$-alkoxy, preferably $C_1$–$C_2$-alkoxy group, preferably a methyl, ethyl, β-cyanoethyl or β-($C_1$–$C_2$-alkoxy)-ethyl radical, $R_5$ represents a $C_1$–$C_4$-alkyl radical which is optionally substituted by a halogen atom, preferably a chlorine atom, or a nitrile group, preferably a methyl, ethyl or β-chloroethyl radical, $R_6$ represents a $C_1$–$C_6$-alkyl radical, $R_7$ repesents a $C_1$–$C_4$-alkyl radical, preferably a $C_1$–$C_2$-alkyl radical, which is optionally substituted by a halogen atom, preferably a chlorine atom, X represents hydrogen, chlorine or bromine and $An^-$ represents an anion.

Amongst the dyestuffs of the formula II, preferred dyestuffs are, in turn, those
in which
$R_4$ repesents methyl, ethyl or β-cyanoethyl,
$R_5$ represents methyl, ethyl or β-chloroethyl,
$R_6$ represents $C_1$–$C_4$-alkyl and
$R_7$ represents methyl and
X and $An^-$ have the indicated meaning;
particularly preferred dyestuffs of the formula II are those in which
$R_4$ and $R_5$ represent methyl or ethyl,
$R_6$ and $R_7$ represent methyl and
X represents chlorine or bromine.

The dyestuffs of the formula I can be prepared according to various processes:

Process A

By condensation of a compound of the formula

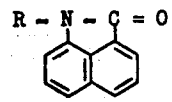 (III)

in which
R has the meaning indicated under the formula I
with an amine of the formula

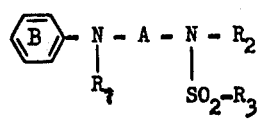 (IV)

in which
$R_1$, $R_2$, $R_3$ and A have the meaning indicated under the formula I,
in the presence of condensation agents, such as phosphorus oxychloride, advantageously with the addition of phosphorus pentoxide, phosphorus pentachloride or aluminium chloride, at temperatures between about 60°C and the boiling point of the mixture. The phosphorus oxychloride is employed in an amount of at least 0.5 mol per mol of compound of the formula III or IV. The condensation is preferably carried out with an excess of phosphorus oxychloride. The chloride then simultaneously serves as the condensation agent and diluent. However, the reaction can also be carried out in organic solvents which are inert under the reaction conditions, for example halogenohydrocarbons, such as chloroform, carbon tetrachloride, perchloroethylene, chlorobenzene and dichlorobenzene.

Process B

By reaction of compounds of the formula

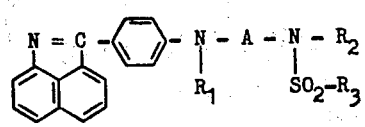 (V)

in which
$R_1$, $R_2$, $R_3$ and A have the meaning indicated under the formula I
with quaternising agents which are able to donate, or form, the radical R. The quaternisation is carried out in a manner which is in itself known. The quaternising agents, which react with splitting off of the radical R and of an anionic radical $An^{(-)}$, are employed at temperatures of 0° to 150°C, preferably 50°–120°C, optionally in the presence of acid-binding compounds, such as alkaline earth metal oxides, for example magnesium oxide or calcium oxide, alkali metal carbonates and alkaline earth metal carbonates, for example sodium bicarbonate, sodium carbonate, potassium carbonate or calcium carbonate, or acetates, for example sodium acetate or potassium acetate, and optionally in diluents which are largely inert under the reaction conditions, such as water or organic solvents, for example hydrocarbons, such as benzene, nitrobenzene, toluene or xylene, halogenohydrocarbons, such as chloroform, carbon tetrachloride, tetrachloroethylene, chlorobenzene or dichlorobenzene, aliphatic ketones, for example acetone or methyl ethyl ketone, and also dimethylformamide, acetonitrile, glacial acetic acid, formic acid and alcohols, for example ethanol, propanol and butanol.

The following may be mentioned as examples of representatives of these quaternising agents: alkyl halides, such as methyl iodide, ethyl bromide, butyl iodide, 2-bromopropionic acid amide, chloroacetic acid ethyl ester, chloroacetic acid amide or 2-bromopropionitrile, alkenyl halides, such as allyl chloride, allyl bromide or methallyl bromide, cycloalkyl halides, such as cyclohexyl bromide, aralkyl halides, such as benzyl chloride or 4-methylbenzyl bromide, alkyl sulphates, such as dimethyl sulphate or diethyl sulphate, and arylsulphonic acid alkyl esters, such as toluenesulphonic acid methyl ester, ethyl ester, n-propyl ester, 2-chloroethyl ester or 2-cyanoethyl ester.

Quaternising agents which form the radical R by addition in the presence of an acid which forms the anion $An^{(-)}$ are reacted with the compounds of the formula V at temperatures of 50° to 100°C in the presence of an organic or inorganic acid which provides the anion $An^{(-)}$, for example formic acid, acetic acid or hydrochloric acid, optionally in an organic solvent which is inert under the reaction conditions, such as benzene, toluene, xylene, chlorobenzene or dichlorobenzene, nitrobenzene, dioxane, chloroform, dimethylformamide or N-methylpyrrolidone. These quaternising agents include, for example, unsaturated compounds which have an activating group in the position adjoining the double bond, such as acrylic acid and methacrylic acid and their derivatives, for example esters, such as acrylic acid methyl ester and methacrylic acid ethyl ester, amides, such as acrylamide, N-methylacrylamide and methacrylamide, or nitriles, such as acrylonitrile and methacrylonitrile.

Process C

By acylation of dyestuffs of the formula

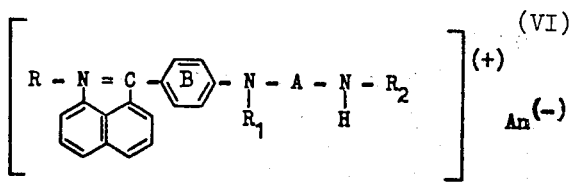

in which
R, $R_1$, $R_2$ and A have the meaning indicated under the formula I
with reactive derivatives of sulphonic acids, for example with sulphochlorides of the formula $$R_3SO_2Cl \qquad \text{(VIII)}$$

in which
$R_3$ has the meaning indicated under the formula I.

This acylation is preferably carried out in an aqueous medium, preferably in the presence of acid-binding materials. As examples of these there may be mentioned: inorganic acid-binding agents, such as alkali metal carbonates and alkaline earth metal carbonates, for example sodium carbonate or potassium carbonate and calcium carbonate, or alkaline earth metal oxides, for example magnesium oxide and calcium oxide, and organic acid-binding agents, such as tertiary amines, for example triethylamine, diethylaniline and pyridine.

However, the acylation can also be carried out in organic solvents, preferably polar organic solvents, such as dimethylformamide, dimethylsulphoxide, acetonitrile and N-methylpyrrolidone.

Examples of suitable compounds of the formula III are: N-methyl-, N-ethyl-, N-iso-propyl-, N-n-propyl-, N-iso-butyl-, N-n-butyl-, N-iso-amyl-, N-n-hexyl-, N-cyclohexyl-, N-2-trimethylene-, N-benzyl-, N-$\beta$-phenylethyl-, N-$\gamma$-phenylpropyl-, N-phenyl-, N-4'-methylphenyl-, N-4'-methylbenzyl-, N-$\beta$-cyanoethyl-, N-$\beta$-chloroethyl-, N-$\beta$-methoxyethyl-, N-$\beta$-methoxycarbonylethyl-, N-ethoxycarbonylmethyl- and N-allyl-naphtholactam-(1,8), their monochloro and monobromo derivatives which are substituted in the naphthalene ring in the p-position to the nitrogen, 4-methoxy-, 4-ethoxy-, 4-hydroxy-, 4-acetylamino-, 4-dimethylamino-, 4-methylsulphonylamino-, 4-amidosulphonyl-, 4-dimethylamidosulphonyl-, 4-cyano- and 4-methylmercapto-N-ethyl-naphtholactam-(1,8), 4,5-dichloro-N-methyl-naphtholactam-(1,8), 2,4-dibromo-N-ethyl- and N-n-butyl-naphtholactam-(1,8), 6-methylamino-N-methyl-naphtholactam-(1,8) and 2-ethyl-N-methylnaphtholactam-(1,8).

Examples of suitable compounds of the formula IV are the aniline derivatives of the formula

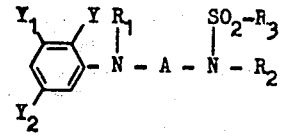 IV a listed in the table which follows:

| A | $R_1$ | $R_2$ | $R_3$ | Y | $Y_1$ | $Y_2$ |
|---|---|---|---|---|---|---|
| —$CH_2$—$CH_2$— | Methyl | Methyl | Methyl | Hydrogen | Hydrogen | Hydrogen |
| " | Hydrogen | " | " | Methyl | " | " |
| " | " | " | " | Methoxy | " | " |
| " | " | " | " | " | " | Methoxy |
| " | Ethyl | " | " | Hydrogen | Methyl | Hydrogen |
| " | " | Ethyl | Chloromethyl | " | Hydrogen | " |
| " | Isopropyl | n-Propyl | $\beta$-Chloroethyl | " | " | " |
| " | n-Propyl | n-Butyl | -Chlorobutyl | " | " | " |
| " | Isobutyl | Hydrogen | Dimethylamino | " | " | " |
| " | $\beta$-Chloroethyl | Trimethylenesultam | | " | " | " |
| " | Methyl | Tetramethylenesultam | | " | " | " |
| " | Isoamyl | Methyl | Methyl | " | Chlorine | " |
| " | Neopentyl | " | " | " | Methoxy | " |
| " | n-Hexyl | " | " | " | Hydrogen | " |
| " | Ethyl | Cyclohexyl | " | " | " | " |
| " | " | Benzyl | " | " | " | " |
| " | " | $\beta$-Phenylethyl | " | " | " | " |
| " | " | Phenyl | " | " | " | " |
| " | " | 4-Methylphenyl | " | " | " | " |
| " | " | 4-Methoxyphenyl | " | " | " | " |
| " | " | $\alpha$-Pyridyl | " | " | " | " |
| " | " | 2-Thiazolyl | " | " | " | " |
| " | " | 2-Benzthiazolyl | " | " | " | " |
| " | " | 3-Tetramethylene-sulphonyl | " | " | " | " |
| " | " | 3-(1,2,4-Triazolyl) | " | " | " | " |
| —$CH_2CH_2CH_2$— | Methyl | Methyl | " | " | " | " |
| —CH—$CH_2$—<br>\|<br>$CH_3$ | " | " | " | " | " | " |
|    $CH_3$<br>   \|<br>—$CH_2$—C—<br>   \|<br>   $CH_3$ | | | | | | |
| —$CH_2CH_2CH_2CH_2$— | " | " | " | " | " | " |
| —$CH_2$—$CH_2$— | Ethyl | $\beta$-Methoxyethyl | " | " | Methoxycarbonylamino | " |
| " | $\beta$-Methoxyethyl | $\gamma$-Chloropropyl | " | " | Ethoxycarbonylamino | " |
| " | $\beta$-Cyanoethyl | $\beta$-Ethoxyethyl | " | " | Hydrogen | " |
| " | $\beta$-Methylsulphonyl-methyl-amino-ethyl | Methyl | | | | |
| —$CH_2$—$CH_2$ | $\beta$-Chloroethyl | $\beta$-(Methylsulphonyl)-methylamino-ethyl | " | " | " | " |

| A | $R_1$ | $R_2$ | $R_3$ | Y | $Y_1$ | $Y_2$ |
|---|---|---|---|---|---|---|
| " | Methyl | Methyl | Cyclohexyl | " | " | " |
| " | " | " | Benzyl | " | " | " |
| " | " | " | Phenyl | " | " | " |
| " | " | " | 4-Methylphenyl | " | " | " |
| " | " | " | 4-Chlorophenyl | " | " | " |

Further suitable compounds of the formula IV are the α-naphthylamine derivatives of the formula

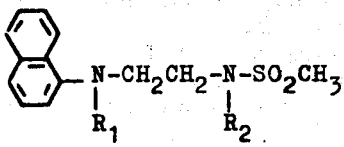

which are listed in the table which follows:

| $R_1$ | $R_2$ |
|---|---|
| $CH_3$ | $CH_3$ |
| $C_2H_5$ | $CH_3$ |
| $CH_2CH_2OH$ | $CH_3$ |
| $CH_2CH_2CN$ | $CH_3$ |
| $CH_2CH_2-OCH_3$ | $CH_3$ |
| $CH_2CH_2-COOCH_3$ | $CH_3$ |
| $CH_3$ | $C_2H_5$ |
| $CH_3$ | $n-C_3H_7$ |
| $C_2H_5$ | $n-C_4H_9$ |
| $C_2H_5$ | $i-C_3H_7$ |
| $CH_2CH_2CN$ | $C_2H_5$ |

The aniline and naphthylamine derivatives are obtainable according to processes which are in themselves known, say by condensation of compounds of the formula

in which
  halogen above all represents a chlorine or bromine atom,
  A and $R_1$ have the meaning indicated under the formula I and
  Y, $Y_1$ and $Y_2$ have the meaning indicated in the table,
with sulphonamides of the formula

in which
  $R_2$ and $R_3$ have the meaning indicated under the formula I
or their alkali metal salts, or by condensation of compounds of the formula

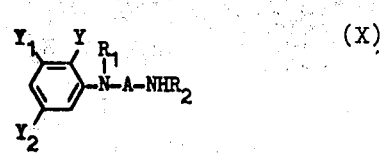

in which
  $R_1$ and $R_2$ have the meaning indicated under the formula I and
  Y, $Y_1$ and $Y_2$ have the meaning indicated in the table,
with the corresponding sulphochlorides.

A further process for the preparation of compounds of the formula IV is to condense an aniline derivative of the formula

in which
  $R_1$ has the meaning indicated under the formula I,
with a compound of the formula

in which
  $R_2$, $R_3$ and A have the meaning indicated under the formula I.

Compounds of the formula XII are obtainable by reaction of aminoalcohols of the formula

with at least two mols of a sulphochloride (VII) in the presence of an acid-binding agent, such as magnesium oxide or calcium oxide, calcium carbonate, dimethylaniline or triethylamine.

The new cationic dyestuffs of the formula I are suitable for dyeing, printing and bulk dyeing of natural and synthetic materials. In particular, they are suitable for dyeing flock, fibres, filaments and tapes, above all of textile materials consisting of polyacrylonitrile, of asymmetrical dicyanoethylene, of copolymers, containing at least 85% by weight of acrylonitrile, of acrylonitrile with other vinyl compounds, such as vinyl chloride, vinylidene chloride, vinyl fluoride, vinyl acetate, vinylpyridine, vinylimidazole, vinyl alcohol, acrylic acid esters and amides and methacrylic acid esters and amides, and also of other synthetic materials modified by anionic groups, especially of anionically modified aromatic polyesters and anionically modified polyamide. Examples of anionically modified aromatic polyesters are polycondensation products of sulphoterephthalic acid and ethylene glycol, that is to say polyethylene glycol terephthalates containing sulphonic acid groups (type DACRON 64 of E.I. DuPont de Nemours and Company), such as are described in Belgian Pat. Spec. No. 549,179 and U.S. Pat. No. 2,893,816.

The dyestuffs according to the invention are distinguished by their very good fastness to light coupled with high economy in use and clarity of colour shade. Further valuable properties which should be singled out particularly are their ease of combination with commercially available dyestuffs, their high levelling capacity, which permits the production of level dyeings even on materials which have high affinity and are not completely homogeneous, their good solubility in water and organic solvents and the fact that concomitant fibres, above all wool, are reserved.

The parts indicated in the examples which follow are parts by weight, unless stated otherwise.

EXAMPLE 1

276 Parts of N-ethyl-4-bromo-naphtholactam-(1,8) are stirred with 1,000 to 1,250 parts of phosphorus oxychloride and 150 parts of phosphorus pentoxide. 256 parts of the compound

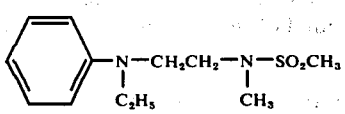

are added to the mixture at 70° to 80°C. The deep blue mixture is kept at 80°C for 12 hours and is then poured into about 10,000 parts of ice water.

After completion of hydrolysis of the phosphorus oxychloride, 1,500 parts of concentrated sodium hydroxide solution are added to the suspension obtained.

The dyestuff of the formula

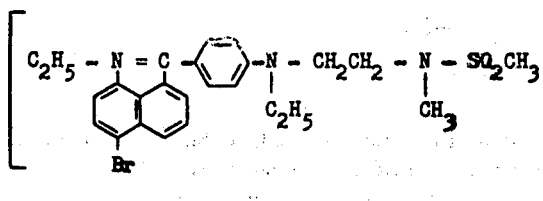

which has separated out in almost quantitative yield is filtered off and washed with dilute sodium chloride solution.

It can be recrystallised from water (about 4,000 parts). It dyes polyacrylonitrile in a reddish-tinged blue. The dyeing is distinguished by outstanding fastness to light.

The aniline used was prepared in accordance with the following processes:

a. 183 g of N-ethyl-N-β-chloroethyl-aniline and 109 g of methanesulphonic acid methylamide in 500 ml of diethylene glycol dimethyl ether were heated in 60 g of potassium hydroxide for 3 hours to 110°C. The reaction mixture was diluted with water and the oil which separated out was separated off, washed with water and distilled. The sulphonamide is obtained in the form of a viscous colourless oil which boils at about 170°C/0.2 mm.

b. 183 g of N-ethyl-N-β-chloroethylaniline and 700 g of 32% strength aqueous methylamine solution were heated to 140°C in an autoclave for 45 minutes. In the course thereof, the pressure assumes a value of about 8 atmospheres gauge.

After cooling, the layer of oil was separated off and freed from excess methylamine and from water by heating under reduced pressure. The resulting crude product contains (according to analysis by gas chromatography) 97% of the compound of the formula

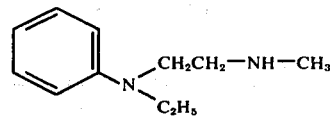

The yield is about 90% of theory.

115 g of methanesulphochloride were added dropwise to 185 g of this crude product at 60° to 80°C. After stirring for a further 1 to 2 hours at 80°C, 500 g of water were added and the mixture was rendered alkaline with sodium hydroxide solution. The oil which separates out was separated off and purified by vacuum distillation.

If instead of the N-ethyl-N-[2-(N'-methyl-N'-methanesulphonylamino)-ethyl]-aniline employed, the equivalent amount of an aniline of the formula

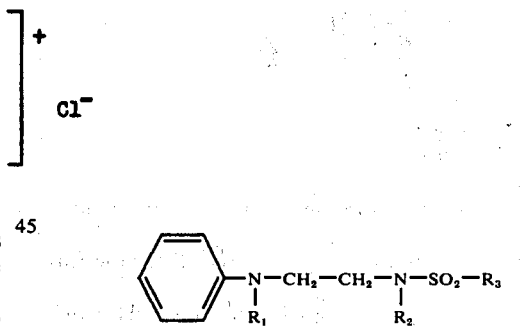

in which

R$_1$, R$_2$ and R$_3$ have the meaning indicated in the table which follows was used for the preparation of the dyestuff, the dyestuffs listed in the table were obtained, which are also distinguished by very good tinctorial properties, for example fastness to light.

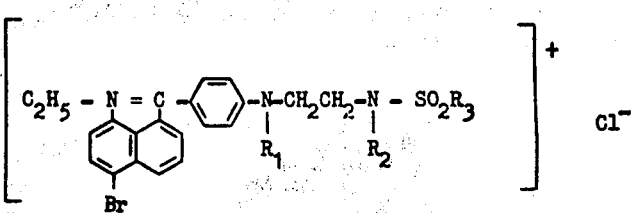

| Example | $R_1$ | $R_2$ | $R_3$ | Colour shade |
|---|---|---|---|---|
| 2 | Methyl | Methyl | Methyl | strongly reddish-tinged blue |
| 3 | n-Propyl | " | " | reddish-tinged blue |
| 4 | iso-Propyl | " | " | " |
| 5 | n-Butyl | " | " | " |
| 6 | Ethyl | Ethyl | Chloromethyl | " |
| 7 | " | Methyl | Ethyl | " |
| 8 | " | " | n-Butyl | " |
| 9 | " | " | Benzyl | " |
| 10 | " | " | Phenyl | " |
| 11 | " | " | p-Tolyl | " |
| 12 | Hydrogen | iso-Butyl | Methyl | strongly reddish-tinged blue |
| 13 | Ethyl | Hydrogen | " | " |
| 14 | n-Hexyl | Methyl | Dimethylamino | " |

EXAMPLE 15

300 Parts of the aniline of the formula

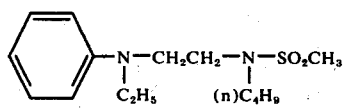

are stirred with 1,500 parts of phosphorus oxychloride and 200 parts of phosphorus pentoxide. 197 parts of N-ethylnaphtholactam-(1,8) are allowed to run into this mixture at 80° to 90°C from a heated vessel and the whole is subsequently stirred for a further 8 hours at 80° to 90°C. It is then worked up in accordance with the instructions in Example 1.

The blue-violet dyestuff of the formula

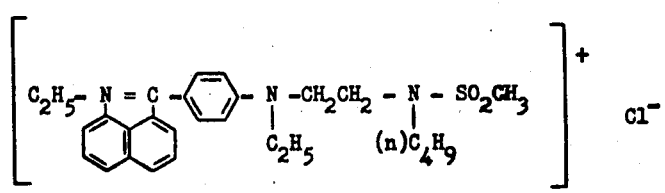

is obtained, which gives dyeings and prins of excellent fastness on polyacrylonitrile.

If instead of N-ethyl-naphtholactam the equivalent amount of N-methyl-, N-β-cyanoethyl-, N-β-chloroethyl-, N-n-propyl-, N-iso-propyl-, N-n-butyl- or N-iso-amyl-naphtholactam was used, equivalent dyestuffs were obtained.

If instead of the N-ethyl-N-[2-(N'-n-butyl-N'-methanesulphonyl-amino)-ethyl]-aniline used, the equivalent amount of an aniline of the formula

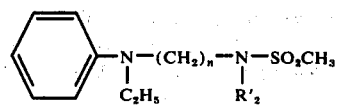

in which $n$ and $R_2'$ have the meaning indicated in the table which follows was employed, valuable blue-violet dyestuffs were again obtained.

| $n$ | $R'_2$ |
|---|---|
| 3 | $CH_3$ |
| 3 | $C_2H_5$ |
| 4 | $CH_3$ |
| 4 | $C_2H_5$ |
| 3 | $C_4H_9 n$ |

EXAMPLE 16

Polyacrylonitrile fibres are introduced, using a liquor ratio of 1:40, into an aqueous bath at 40°C, which contains, per liter, 0.75 g of 30% strength acetic acid, 0.38 g of sodium acetate and 0.15 g of the dyestuff described in Example 1. The bath is heated to the boil over the course of 20 to 30 minutes and is kept at this temperature for 30 to 60 minutes.

After rinsing and drying, a reddish-tinged blue dyeing with outstanding fastness properties is obtained.

EXAMPLE 17

A polyacrylonitrile woven fabric is printed with a printing paste which was prepared as follows: 330 parts of hot water are poured over 30 parts of the dyestuff described in Example 1, 50 parts of thiodiethylene glycol, 30 parts of cyclohexanol and 30 parts of 30% strength acetic acid and the resulting solution is added to 500 parts of crystal gum (gum arabic as thickener). Finally, 30 parts of zinc nitrate solution are also added.

The resulting print is dried, steamed for 30 minutes and then rinsed. A reddish-tinged blue print with very good fastness properties is obtained.

EXAMPLE 18

Acid-modified polyethylene glycol terephthalate fibres are introduced, using a liquor ratio of 1:40, into an aqueous bath at 20°C which contains, per liter, 3 to 10 g of sodium sulphate, 0.1 to 1 g of oleyl alcohol polyglycol ether (50 mols of ethylene oxide per mol of oleyl alcohol), 0 to 15 g of dimethylbenzyldodecylammonium chloride and 0.15 g of the dyestuff described in Example 1 and has been adjusted to pH 4 to 5 with acetic acid.

The bath is heated to 100°C over the course of 30 minutes and is kept at this temperature for 60 minutes. The fibres are then rinsed and dried.

A reddish-tinged blue dyeing with very good fastness properties is obtained.

EXAMPLE 19

Acid-modified synthetic polyamide fibres are introduced, using a liquor ratio of 1:40, into an aqueous bath at 40°C which contains, per liter, 10 g of sodium acetate, 1 to 5 g of oleyl alcohol polyglycol ether (50 mols of ethylene oxide per mol of oleyl alcohol) and 0.3 g of the dyestuff described in Example 1 and which has been adjusted to pH 4 to 5 with acetic acid. The bath is heated to 98°C over the course of 30 minutes and is kept at this temperature. The fibres are then rinsed and dried.

A reddish-tinged blue dyeing with very good fastness properties is obtained.

I claim:
1. Dyestuff of the formula

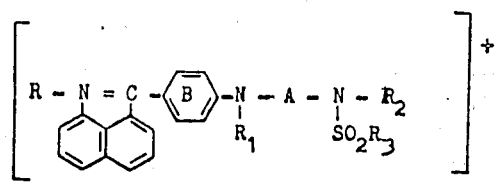

in which
R is $C_1$–$C_6$-alkyl, $C_3$–$C_6$-alkenyl, $C_3$–$C_6$-haloalkenyl, ethylene bonded to the β-position of the naphthalene ring, or $C_1$–$C_6$-alkyl substituted by halogen, $C_1$–$C_4$-alkoxy, cyano, $C_1$–$C_4$-alkoxycarbonyl, or carbonamide;
$R_1$ is hydrogen, $C_1$–$C_6$-alkyl, $C_3$–$C_6$-alkenyl, $C_3$–$C_6$-haloalkenyl, alkylene selected from the group consisting of —$CH_2$—$CH_2$—($CH_2$)$_3$—, —$CH_2$—$CH(CH_3)$—$CH(CH_3)$—, and —$CH_2$—$CH_2$—$CH(CH_3)$— bonded to ring B in the 0-position or $C_1$–$C_6$-alkyl substituted by halogen, $C_1$–$C_4$-alkoxy, cyano, $C_1$–$C_4$-alkoxycarbonyl, or carbonamide;
$R_2$ is hydrogen, $C_1$–$C_6$-alkyl, $C_1$–$C_6$-alkyl substituted by halogen or $C_1$–$C_4$-alkoxy, $C_3$–$C_6$-alkenyl, $C_3$–$C_6$-haloalkenyl, cyclopentyl, cyclohexyl, halocyclopentyl, halocyclohexyl, $C_1$–$C_4$-alkylcyclopentyl, $C_1$–$C_4$-alkylcyclohexyl, phenyl, halophenyl, $C_1$–$C_4$-alkylphenyl, $C_1$–$C_4$-alkoxyphenyl, nitrophenyl, cyanophenyl, pyridinyl pyrimidinyl, triazinyl, triazolyl, thiazolyl, imidazolyl, tetrazolyl, benzyl, 2-phenylethyl, 2-phenylpropyl-(2) or any of said benzyl, 2-phenylethyl, or 2-phenylpropyl-(2) sub-stituted in the phenyl nucleus by halogen, $C_1$–$C_4$-alkyl, or $C_1$–$C_4$-alkoxy;
$R_3$ is $C_1$–$C_6$-alkyl, $C_1$–$C_6$-alkyl substituted by halogen, $C_1$–$C_4$-alkoxy, cyano, $C_1$–$C_4$-alkoxycarbonyl, or carbonamide, $C_3$–$C_6$-alkenyl, $C_3$–$C_6$-haloalkenyl, cyclopentyl, cyclohexyl, halocyclopentyl, halocyclohexyl, $C_1$–$C_4$-alkylcyclopentyl, $C_1$–$C_4$-alkylcyclohexyl, phenyl, halophenyl, $C_1$–$C_4$-alkylphenyl, $C_1$–$C_4$-alkoxyphenyl, nitrophenyl, cyanophenyl, pyridinyl, pyrimidinyl, triazinyl, triazolyl, thiazolyl, imidazolyl, tetrazolyl, di-$C_1$–$C_4$-alkylamino, morpholino, piperidino, piperazino, benzyl, 2-phenylethyl, 2-phenylpropyl-(2) or any of said benzyl, 2-phenylethyl, or 2-phenylpropyl-(2) substituted in the phenyl nucleus by halogen, $C_1$–$C_4$-alkyl, or $C_1$–$C_4$-alkoxy;
$R_2$ and $R_3$, additionally may be joined together to form a cyclic sulphonamido;
A is $C_2$–$C_4$-alkylene;
An $^{(-)}$ is an anion;
Ring B may be fused to another benzene ring; and the cyclic and acyclic radicals in the above formula may be further substituted by $C_1$–$C_4$-alkoxy, β-methoxyethoxy, β-cyanoethoxy, allyloxy, halogen, amino, $C_1$–$C_4$-alkylamino, benzylamino, acetylamino, methylsulphonylamino, phenylsulphonylamino, dimethylamino, phenylamino, methylsulphonyl, phenylsulphonyl, methoxycarbonyl, ethoxycarbonyl, carbamoyl, or cyano, and the cyclic radicals may additionally be substituted by $C_1$–$C_4$-alkyl.
2. Dyestuff of claim 1 of the formula

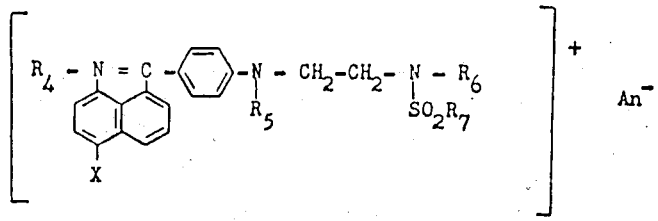

in which
$R_4$ is $C_1$–$C_4$-alkyl or $C_1$–$C_4$-alkyl substituted by a cyano or $C_1$–$C_4$-alkoxy;
$R_5$ is $C_1$–$C_4$-alkyl or $C_1$–$C_4$-alkyl substituted by halogen;
$R_6$ is $C_1$–$C_6$-alkyl;
$R_7$ is $C_1$–$C_4$-alkyl or $C_1$–$C_4$-alkyl substituted by halogen;
X is hydrogen, chlorine, or bromine; and
An $^-$ is an anion.
3. Dyestuff according to claim 2, characterised in that
$R_4$ represents methyl, ethyl, β-cyanoethyl or β-($C_1$–$C_2$-alkoxy)-ethyl,
$R_5$ represents methyl, ethyl or β-chloroethyl and
$R_7$ represents a $C_1$–$C_2$-alkyl or $C_1$–$C_2$-chloroalkyl.
4. Dyestuff according to claim 2, characterised in that
$R_4$ represents methyl, ethyl or β-cyanoethyl,
$R_5$ represents methyl, ethyl or β-chloroethyl,
$R_6$ represents $C_1$–$C_4$-alkyl and
$R_7$ represents methyl.
5. Dyestuff according to claim 2, characterised in that $R_4$ and $R_5$ independently of one another represent
methyl or ethyl,
$R_6$ and $R_7$ represent methyl and
X represents chlorine or bromine.
6. Dyestuff according to claim 1 of the formula
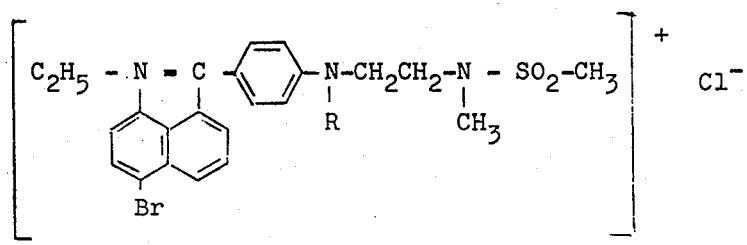
in which R represents methyl, ethyl, n-propyl or isopropyl.
7. Dyestuff according to claim 1 of the formula
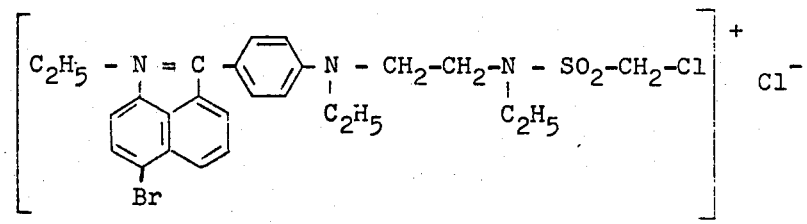
* * * * *